United States Patent [19]

Oberto et al.

[11] Patent Number: 5,336,609
[45] Date of Patent: Aug. 9, 1994

[54] TRANSFORMED YEASTS FOR PRODUCING LYSOZYME, PLASMIDS USED FOR THIS TRANSFORMATION, METHOD OF PRODUCING LYSOZYME

[75] Inventors: Jacques Oberto, Steenokkerzeel; John R. N. Davison, Brussels, both of Belgium

[73] Assignee: Labofina, S.A., Belgium

[21] Appl. No.: 804,774

[22] Filed: Dec. 5, 1989

[30] Foreign Application Priority Data

Dec. 6, 1984 [BE] Belgium ............................ 0/214124

[51] Int. Cl.$^5$ ...................... C12N 15/56; C12N 15/81
[52] U.S. Cl. ................................ 435/206; 435/172.3; 435/320.1; 435/254.21
[58] Field of Search ...................... 435/172.3, 206, 255, 435/171, 91, 68, 320, 942, 940; 935/28, 37, 48, 60

[56] References Cited

U.S. PATENT DOCUMENTS

3,515,643 6/1970 Gbielmetti et al. ................ 435/206
3,852,476 12/1974 Nagano ................................ 426/7

FOREIGN PATENT DOCUMENTS

0100561 2/1984 European Pat. Off.
120551 10/1984 European Pat. Off.
2116567 9/1983 United Kingdom.

OTHER PUBLICATIONS

Hitzeman et al, 1983 Science 219:620-625.
Gene, 11 (12980) 11-19, Chevalier et al.
Gene, 34 (1985) 363,366, Heuterspreute et al.
Gene, 8 (1975) 121-133, Broach et al.
McKenney et al, "A System to Study Promoter and Terminator Signals by E. Coli . . . ".
Gene Amplification and Analysis pp. 383-415 (1981).
Cloning with 2-μm DNA Vectors and the Expression of Foreign Genes in Saccharomyces cerevisiae, Dusseldorf, 96 Curr. Tpo. Microbiol. Immunol., (1982) 119-144, C. P. Hollenberg.

Herbert et al., "Chemical Analysis of Microbial Cells," Methods in Microbiology 209-344 (1971).
Nucleic Acids Research "Cloning of chicken lysozyme structural gene sequences in vitro", vol. 5, No. 9, Sep. 1978, pp. 3275-3294.
J. Mol. Biol. "Efficient expression of cloned complementary DNAs for secretory proteins after injection into Xenopus oocytes", P. Krieg et al, 1984, 180(3), pp. 615-643.
Science "Disulfide bond engineered into T4 lysozyme: Stabilization of the protein toward thermal inactivation", vol. 226, Nov. 2, 1984, pp. 555-557.
102 Chemical Abstract 126582, 1985.
Anal. Biochem, 63, 414 (1975), Wang et al.
Biochem. Biophys. A, 8, 302, (1952), Shugar.
Nucl. Acids. Res. 10, 2625, (1982) Dobson et al.
Nature, 275, 104, (1978), Beggs.
Nature, 283, 835, (1980), Beggs et al.
J. Biol. Chem., 157, 43, (1945), Alderton et al.
J. Mol. Biol. 49, 639, (1970), McMacken et al.
Cell, 34, 95, (1983), Jayaram et al.
J. Bacteriol., 156, 625,. (1983), Erhart et al.
Nucl. Acids Res., 11, 1645, (1983), Dente et al.
Prikl. Biok. I. Mikrobiol., 18, 529, (1982), Maksimova et al.
EMBO Journal, 1, 1207, (1982), Matthias et al.
Jap. J. Zootech. Sc., 42, 289, (1971), Akashi.

(List continued on next page.)

*Primary Examiner*—Richard A. Schwartz
*Assistant Examiner*—John LeGuyader
*Attorney, Agent, or Firm*—Roger W. Parkhurst; John K. Abokhair; M. Norwood Cheairs

[57] ABSTRACT

Transformed yeasts comprising DNA which include at least one copy of a fragment coding for a 1,4-β-N-acetylmuramidase which is expressed in the yeasts as the corresponding active protein, and a process for preparing lysozyme by growing said transformed yeasts.

38 Claims, 7 Drawing Sheets

OTHER PUBLICATIONS

Molecular and Cellular Biochemistry "What's new in lysozyme research?", 63, 165–189 (1984).
Molecular Genetics in Yeast, "Multiple-copy Yeast Plasmid Vectors", Jean D. Beggs, Imperial Col. of Sci. and Tech., Dept. of Biochem, London (1981).
Mol. Gen. Genet, "Stability of a Cloned Gene in Yeast Grown in Chemostat Culture", (1983), 192:361–365, R. M. Walmsley et al.
J. Ferment Tech., Studies on Egg White Lysozome, vol. 46, No. 10, pp. 782–788 (1968).
Baldacci et al. 1979 *NAR* 6:2667.
Baldacci et al. 1981 *NAR* 9:3575.
Jung et al. 1980 *PNAS* 77:5759.
Grez et al. 1981 Cell 25:743.
Guarente, L. 1983 In: Methods in Enzymology vol. 101: 181–1191.

TRANSFORMED YEASTS FOR PRODUCING LYSOZYME, PLASMIDS USED FOR THIS TRANSFORMATION, METHOD OF PRODUCING LYSOZYME

This invention relates to yeasts which, by transformation with DNA of foreign origin, have been rendered capable of producing enzymes of the 1,4-$\beta$-N-acetylmuramidase type.

BACKGROUND OF THE INVENTION

It is known that 1,4-$\beta$-N-acetylmuramidases are enzymes capable of selectively cleaving the glycosidic bond between N-acetylglucosamine and N-acetylmuramic in the peptidoglycans which form the cell wall of bacteria. This wall is thus lysed, thereby entailing the death of the cells. These enzymes, more commonly called lysozymes, thus act as bactericides, and this property explains their generalized presence in most of the biological fluids of higher animals. Lysozyme is indeed found, at various levels of concentration, in blood, tears, saliva, milk, etc., of mammals. It is also found in the vegetable kingdom, e.g. in papaya. However, industrial-scale extraction of lysozymes is carried out from egg white, where it is present in relatively great concentration, by various absorption and/or precipitation processes. For example, see Belgian patent No. 694,538.

Present applications of chicken lysozymes are mostly in the pharmaceutical area, where it is used to fight various infections. Other applications are in the food industry. For instance, it is known that lysozyme can be used in the manufacture of baked pressed-paste cheese to efficiently inhibit during ripening the development of butyric acid bacteria responsible for manufacturing defects including cheese blowing. For example, see French patent No. 8,003,321. It can also be used for the preservation of various perishable foodstuffs, such as meat products (A. Akashi, Jap. J. Zootechnical Sci. 42, 1971, 289); wines (Japanese patent No. 3115/71, 1971); or sake (M. Yajima et al., J. Ferm. Technol. 46, 1968, 782). It can further be used to preserve milk components for pediatric use (Japanese patent 16780/70, 1970).

These various applications represent a considerable potential market insofar as lysozyme can be produced easily, in large amounts and at a sufficiently low cost. The various processes presently enabling extraction of lysozyme from egg white are commercially acceptable only if the egg white can be reused in food after being treated. Lysozyme production capacity is therefore partly ruled by the egg white market, and this poses a problem more difficult to solve in that technical difficulties, and even in some countries legal restraints, limit the use of treated egg white in standard foodstuffs.

These problems, which are linked to the availability of natural sources of lysozyme, become insurmountable in the case of mammalian lysozymes, whether the initial concentration thereof is too low, as with cow milk lysozyme, or the raw material is practically unavailable, as with human lysozyme. Thus it appears that there is a need for a technique enabling production of lysozyme and avoiding the hereabove described problems.

OBJECTS OF THE INVENTION

The main object of this invention is to provide yeasts made capable of producing lysozyme by genetic engineering—more specifically, yeasts so transformed that their DNA comprises at least one copy of a fragment coding for a 1,4-$\beta$-N-acetylmuramidase and that this fragment is expressed therein as the corresponding active protein. Another object of the invention is to provide yeasts transformed as hereabove described, but which are also capable of excreting the lysozyme they produce, so as to facilitate the separation and the purification thereof. The plasmids ensuring this transformation also form an object of the invention, as does the process for producing lysozyme by growing the transformed yeasts. These objects, as well as other advantages and implications of the invention, will appear more clearly in the description below.

DETAILED DESCRIPTION OF THE PREFERRED EMBODIMENTS OF THE INVENTION

It is known to genetically reprogram yeasts by transforming them with a fragment of DNA carrying a coding part formed by a heterologous gene or by the product of the reverse transcription of the corresponding messenger RNA. For this purpose, it is usual to use as vectors for said fragment plasmids capable of autonomous replication in the yeast cell by the presence of a replication origin recognized by the replication machinery of the host cell. The vector must also comprise a marker gene allowing visualization and selection of the cells which have effectively been transformed by the plasmid. Finally, the coding part must be preceded by a promoter, i.e., a sequence recognized by the RNA polymerase of the host cell, so as to ensure efficient transcription of the coding part into the corresponding messenger RNA.

In practice, these techniques have mainly been applied to yeasts of the species Saccharomyces cerevisiae for which a great number of expression vectors comprising those various elements have been constructed. These vectors generally comprise the replication origin of the 2-micron plasmid present in most of this species, or even as ARS segment of autonomous replication of chromosomal origin. As a marker gene, there is generally used a gene which codes for an enzyme involved in the biosynthesis of an essential metabolite, e.g., an amino acid. In such a case, the host cell to be used is a yeast strain which, through mutation, has become auxotrophic for this metabolite. By inoculating with this strain a medium free from said metabolite, only those cells transformed by a plasmid bearing the missing gene will be able to grow. Typical examples of such markers are the genes LEU2 and TRP1 which respectively code for an enzyme involved in the biosynthesis of leucine and tryptophane. These expression vectors must also comprise one, or preferably several restriction sites, for insertion of the coding part of interest, as well as the various elements required for optimizing the expression thereof, i.e., promoters, terminators, and other control elements.

These plasmids often further comprise bacterial sequences capable of ensuring their replication and their selection in an intermediate bacterial host, e.g., Escherichia coli. As classical examples of such shuttle plasmids, one may cite YEpl3 (J. R. Broach et al. Gene 8, 1979, 121), pFL1-4 (M. R. Chevallier et al, Gene 11, 1980, 11), pJDB207 (J. D. Beggs Alfred Benson Symposium No. 16, Munksgaard, Copenhaegen, 1981, p. 383), pMH158 and pJO158 (M. Heuterspreute et al., Gene, 34, 1985, 363–366).

According to a preferred embodiment of the invention, a plasmid comprising at least the replication (REP)

functions of the sequence of the 2-micron endogenous plasmid is used, mainly when the host cell belongs to the *S. cerevisiae* species. Said functions generally bring to the plasmid a greater stability, particularly if the host cell has beforehand been cured of its 2-micron plasmids (C. P. Hollenberg, Curr. Top. Microbiol. Immunol. 96, 1982, 119; R. M. Walmsley et al., Mol. Gen. Genet. 1983, 361). Classical examples of such vectors are plasmids pJDB219 and pJDB248 (J. D. Beggs, Nature 275, 1978, 104). Another vector of this type is described in the examples given hereafter.

Finally, to ensure an expression level as high as possible of the coding part of interest, it is necessary to associate it with a promoter as efficient as possible. Various strong promoters are known in yeast, e.g., the promoters of alcohol dehydrogenase (ADH1), enolase (ENO8 and ENO46), glyceraldehyde-3-phosphate dehydrogenase (GAP63 and GAP491), phosphoglycerate kinase (PGK) (M. J. Dobson et al., Nucleic Acids Res. 10, 1982, 2625), alkaline phosphate (PHO3 and PHO5) (European patent application no. 100,561) or still the promoter p415 of which mention will be made hereafter.

These various techniques, which have been successfully applied to the cloning and the expression of many heterologous genes in yeast, can be used as well for ensuring expression in yeast of the genes of lysozymes or of any part of DNA coding for a 1,4-β-N-acetylmuramidase. Examples of specific constructions are given in the present patent for the purpose of illustration, but it is evident that many other possibilities exist and that various combinations of replication origins, marker genes, efficient promoters, and other structural elements may be used to obtain similar results. The transformed cells obtained in those various cases must therefore be considered as being within the scope of the invention.

Similarly, although most of these techniques have mainly been applied to the transformation of the yeast *S. cerevisiae*, also comprised in the invention are the transformed cells obtained from other species and genera of yeasts transformable by expression vectors of the same type as those mentioned hereabove and their variants. As examples of other yeasts, one may cite *Sacchoromycopsis lipolytica, Schizosaccharomyces pombe, Kluyveromyces lactis*, etc. However, according to a preferred embodiment, transformable yeasts of the genus Saccharomyces will be used as host cells, and still preferably those belonging to the species *S. cerevisiae*. As examples of transformable strains belonging to this species, one may cite AH22 and GRF18 amongst many others.

The 1,4-β-N-acetylmuramidases produced according to the invention by these various yeasts may have different origins. It may, for example, be chicken lysozyme which, as described above, is already produced on an industrial scale. However, it is evident that DNA parts coding for lysozymes from other sources may similarly be expressed in yeast, as these various lysozymes present, to different extents, marked homologies (P. Jolles et al., Moll. & Cell. Boichemistry 63, 1984, 165). For example, one may express in yeast goose lysozyme, which has a notably higher specific activity than chicken lysozyme (R. C. Canfield et al., in "Lysozyme", ed. E. F. Osserman et al., Academic Press 1974, p.63). One may also express in yeast human lysozyme, also very active and particularly indicated for pharmaceutical uses as well as in the composition of milks for pediatric use.

The lysozyme from papaya, and that coded by bacterial viruses can also be cited.

When, according to the invention, a yeast strain has been induced by genetic engineering to produce lysozyme from one or another origin, it is necessary, to take advantage of this new property, to multiply it by fermentation under the most favorable conditions for its growth. A biomass is thus obtained which can find applications in human or animal feeding. It is known, for example, that yeast autolysates are increasingly used as additives in various foodstuffs (such as meat pie, soups and sauces), not only because of their own nutritive value, but also because of their organoleptic properties. The presence of lysozyme in the original yeasts offers the advantage of preserving to a certain point the autolysates from bacterial contamination, to which they are exposed as are the food products in which they are incorporated. On the other hand, it is known that the presence of lysozyme allows a reduction in the sterilization temperature of food products (see, for example, British patent no. 1,438,560).

Yeasts according to the invention can also be used as a source for purified lysozyme, by separating the lysozyme from the yeast. It is however clear that this operation can present considerable difficulties if the lysozyme is associated within the cell to the other cellular proteins. It is thus an important aspect of the invention to provide yeasts capable of excreting the lysozyme produced, whether it is released in the culture medium from where it will be recovered by classical methods, e.g. by absorption and/or precipitation (see, for example, Belgian patent no. 694,538), or it remains associated to the cell wall from where it will be detached by other methods. Indeed, it has surprisingly been observed that the signal leader sequence of 18 amino acids present at the N-terminal part of prelysozyme and which allows secretion of lysozyme into the lumen of the endoplasmic reticulum of chicken oviduct cells, is also recognized by yeast cells. The following examples show clearly that when the DNA coding for chicken prelysozyme is expressed in yeast, the product of this expression is excreted therefrom. Therefore, fusing the 54-nucleotides fragment coding for this signal sequence with the DNA coding for the structural part of other proteins, including lysozyme from other origins, may result in the excretion of said proteins from the yeast cells where they are produced.

However, the most fundamental and most surprising aspect of the invention is the fact that a lysozyme gene can be expressed in yeast without exerting therein any lethal effect, e.g., by lysis of the cells. The only known example of cloning and expressing a lysozyme gene in a heterologous cell is the cloning of the chicken lysozyme gene in Hela and MCF-7 human cells lines (P. D. Matthias et al., the EMBO J., 1, 1982, 1207), although the expression of the gene was only evidenced by the production of the corresponding messenger RNA and not by production of the protein itself. Now it is known that lysozyme is also capable of attacking the yeast cell walls, mainly by hydrolysis of its chitin component (G. N. Maksimova et al., Prikl. Biochim. Mikroboil. 18, 1982, 529). As it is known that the budding of yeasts is accompanied by the formation of a septum of pure chitin between the bud and the mother-cell, it could be expected that the production and excretion of lysozyme by yeast cells would lead to severe alterations of their multiplicative function. It could also be expected that the regeneration of the cell wall from protoplasts after transformation would be comprised. It is therefore surprising that not only could classical techniques of genetic engineering bring yeasts to express a lysozyme gene, but also that cells thus transformed could produce and excrete lysozyme while actively growing.

The above will appear clearly in the examples which follow. These examples are given solely as illustration, as any other construction leading to the production of any 1,4-β-N-acetylmuramidase by any yeast strain is to be considered as being within the scope of the invention.

BRIEF DESCRIPTION OF THE FIGURES

In the following examples, reference is made to the annexed drawings in which.

EXAMPLE 1

1.1. Construction of a complete cDNA clone of chicken lysozyme: plys10

Figure 1:
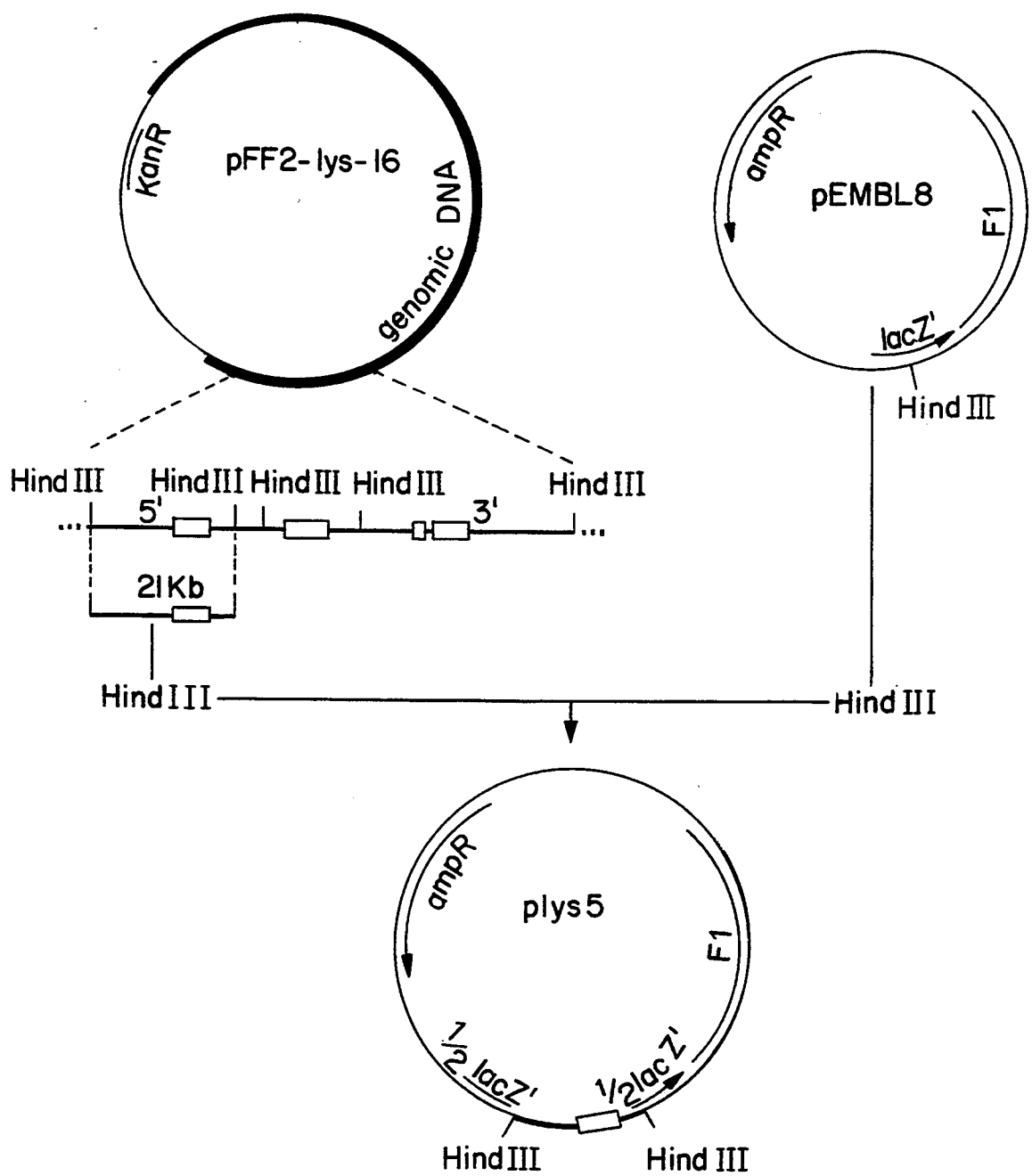
FIG. 1 represents the construction of plasmid plys5 which will later be used for the reconstruction of the complete cDNA of the chicken lysozyme. This construction was started from cosmid pFF2-lys-16 containing a 40 kb insert comprising the entire lysozyme gene. A 2.1 kb HindIII insert comprising the first exon of this gene was then inserted into plasmid pEMBL8. The plys5 plasmid thus obtained is lacZ− and can then be distinguished from plasmid pEMBL8 which is lacZ+.
Figure 2:
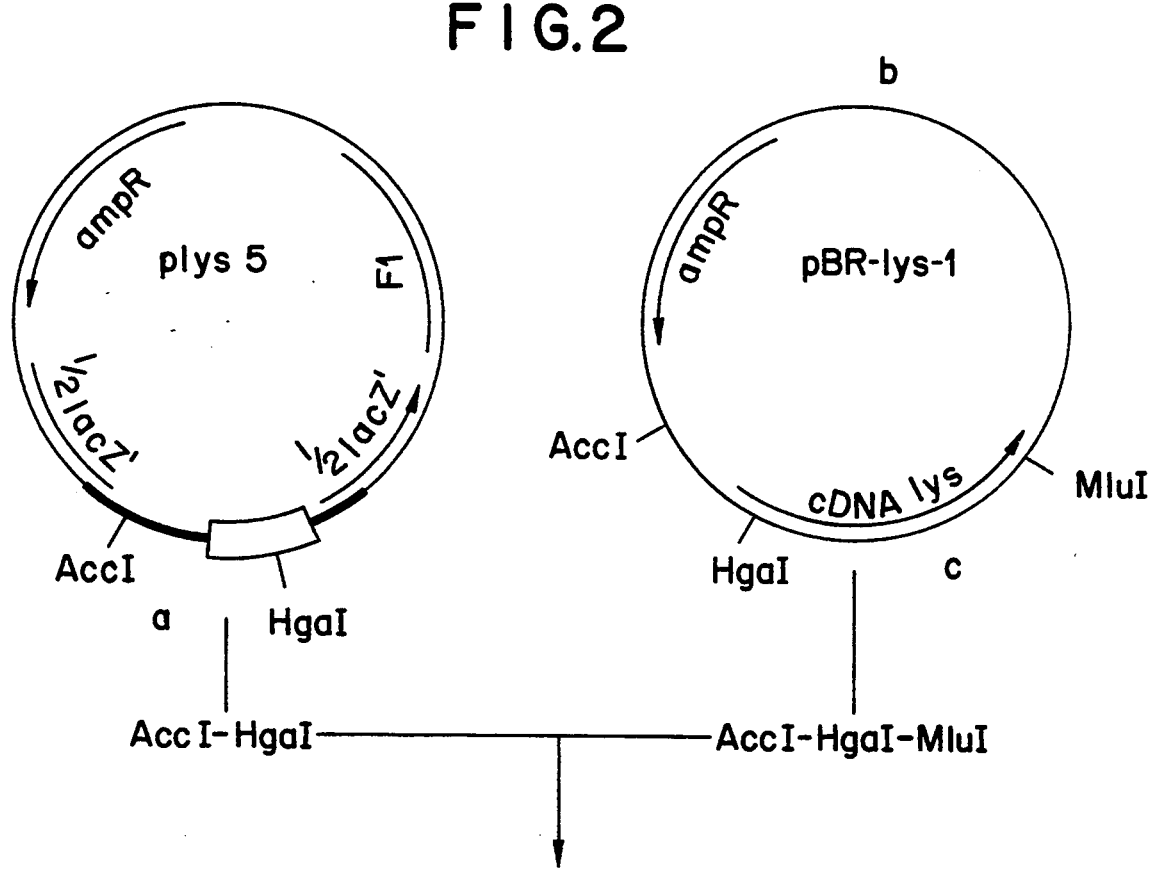
FIG. 2 shows how the complete cDNA of lysozyme has been reconstructed within plasmid plys10 by ligation of a AccI-HgaI fragment originating from plys5 and containing the 5′ terminal end of the lysozyme gene with two other fragments originating from plasmid pBR-lys-1 and containing the remainder of the cDNA of lysozyme.
Figure 2:
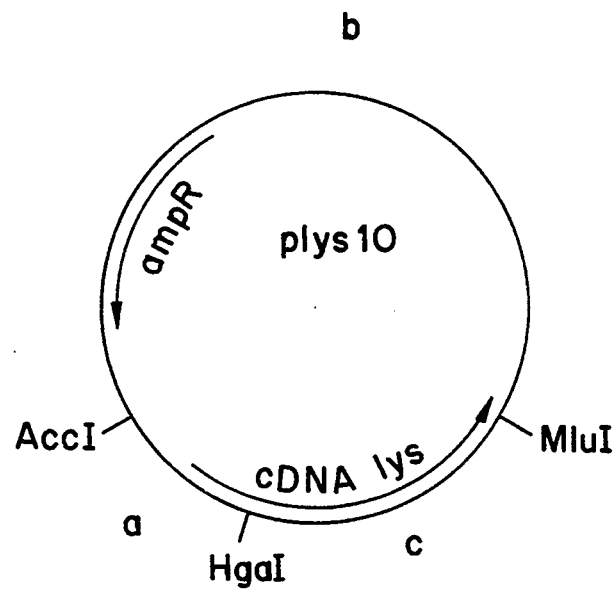

First, the construction of a complete cDNA clone was made, beginning with two different clones: pBR-lys-1 which contains chicken lysozyme cDNA but incomplete at the 5′ end (P. Baldacci et al., Nucleic Acid Res. 6, 1979, 2667), and pFF2-lys-16 which contains 40 kb of chicken genomic DNA comprising the entire lysozyme gene including introns (P. Baldacci et al., Nucleic Acid Res. 9, 1981, 3575) (FIG. 1). Neither of these two clones is suitable for expression of lysozyme in yeast which is unable to correctly process transcripts from higher eucaryotes (J. D. Beggs et al., Nature 283, 1980, 835). It was however possible to reconstruct a complete cDNA clone by combining the 3′ end of the available incomplete cDNA with the 5′ end of the complete gene: it was clear from published data (P. Balducci et al., 1979, op.cit.; A. Jung et al., Proc. Natl. Acad. Sci. USA, 77, 1980, 5759; M. Grez et al., Cell 25, 1981, 743) that the complete gene comprises no introns in the 5′ region corresponding to the missing part of the cDNA. A 2.1 kb DNA fragment from cosmid pFF2-lys-16 was thus sub-cloned into pEMBL8 (L. Dente et al., Nucleic Acid Res. 11, 1983, 1645), giving plasmid plys5 (FIG. 1). This clone contains the complete 5′ proximal exon of the lysozyme gene. A conveniently located HgaI site is present in the region of overlap between plys5 and the cDNA clone pBR-lys-1. A triple ligation involving fragments HgaI-MluI and MluI-AccI of pBR-lys-1 and fragment AccI-HgaI of plys5 enabled the construction of a clone (plys10) containing the entire lysozyme gene, including the ATG initiation codon but without introns (FIG. 2).

1.2. Shortening of the non-translated part of the 5′ area of the lysozyme gene.

The non-coding part of the 5′ region of the lysozyme gene present in plasmid plys10 was deleted by opening the plasmid at the unique AccI restriction site and digestion with BAL31 nuclease. A population of shortened plasmids was thus obtained which were then cleaved at the unique PstI site; the fragments comprised between the PstI site and the end digested by BAL31 were inserted between sites PstI and SmaI of plasmid YEpZ100, as described in Belgian patent no. 901,222. This operation has three consequences:

(1) the non-translated part of the 5′ area preceding the lysozyme ATG codon is deleted;

(2) the AccI and SmaI sites are destroyed; and (3) an easily manipulable BamHI site (immediately adjacent to the SmaI site in YEpZ100) is attached to the beginning of the lysozyme gene.

Figure 3:
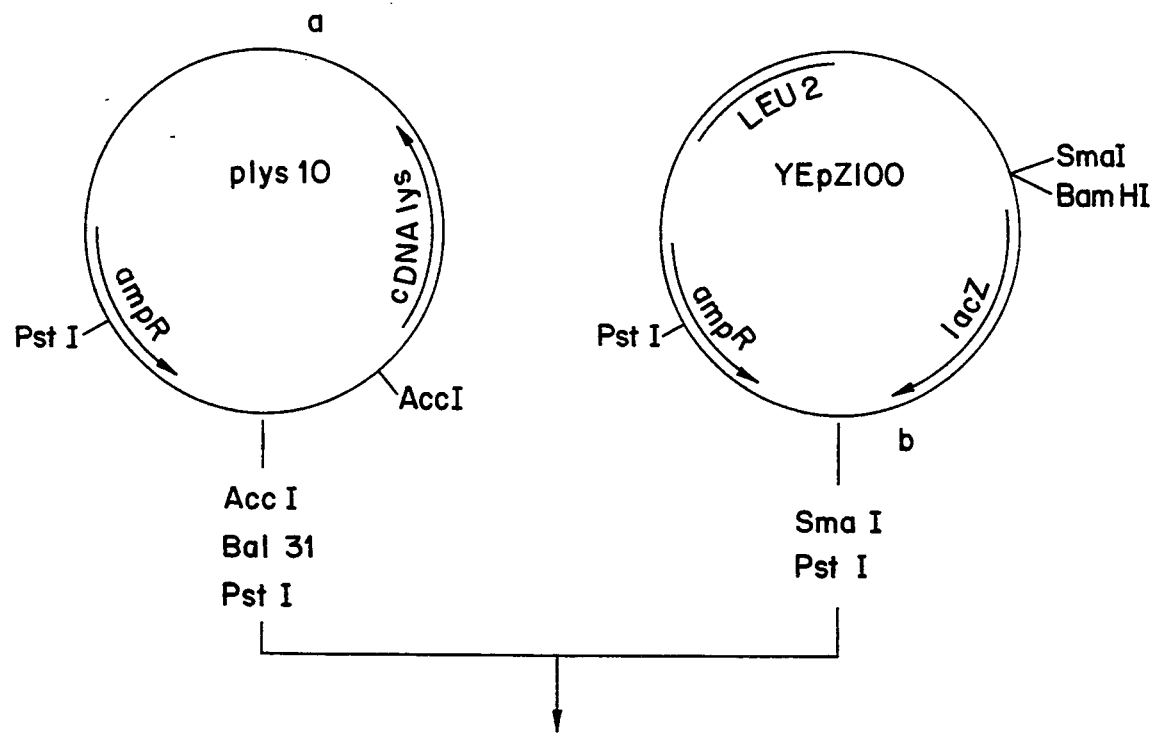
FIG. 3 shows the construction of plasmid plysΔ9 comprising the cDNA of lysozyme deleted by digestion with exonuclease BAL31 of the untranslated part of its 5′ terminal end.
Figure 3:
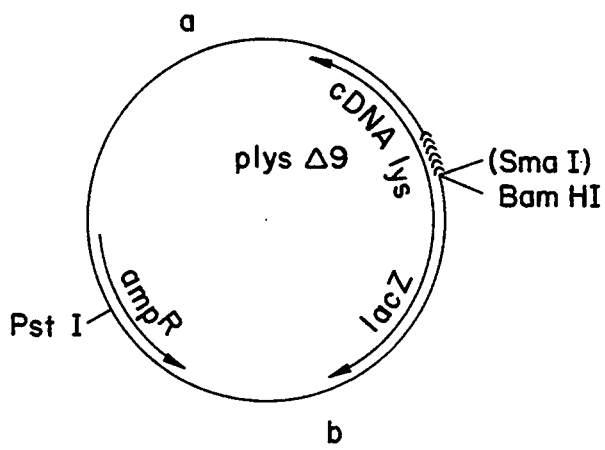

One of the resulting plasmids is called plysΔ9 (FIG. 3).

1.3. Construction of the lysozyme expression vectors.

The complete cDNA of lysozyme is now located between a unique BamHI site at the 5′ end and a unique SphI site at the 3′ end. As said cDNA carries its own ATG initiation codon, the fusion thereof with an ATG-free promoter terminated by a BamHI site should give a functional expression unit that has still to be associated in a plasmid with the replication origin and the β-lactamase gene of pBR322 (to ensure its replication and its selection in E. coli) and with the replication origin of the 2-micron plasmid and the LEU2 gene (for replication and selection in yeast).

Figure 4:
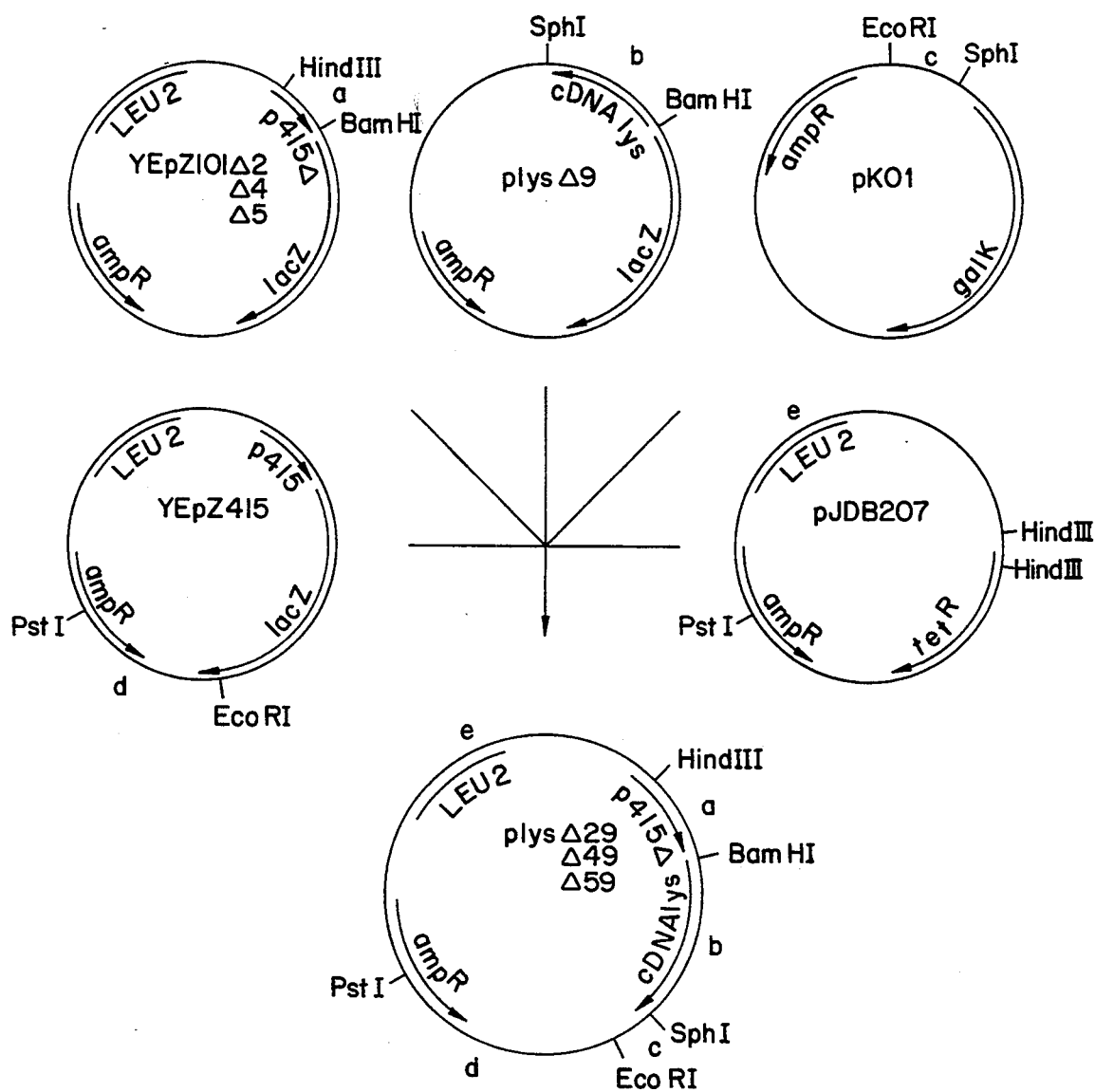
FIG. 4 shows the construction of expression vectors of lysozyme by univocal ligation of purified fragments originating from plasmids YEpZ415, YEpZ101Δ2 (or 4 or 5), plysΔ9, pKO1 and pJDB207. Plasmids plysΔ29 (or 49 or 59) only differ among themselves by the promoters brought by plasmids YEpZ101Δ2 (or 4 or 5) to ensure expression of the lysozyme cDNA brought by plysΔ9.

This construction was carried out by simultaneous ligation of the given following fragments:

(a) a HindIII-BamHI fragment from plasmid YEpZ101Δ2 and comprising the p415Δ2 fragment originating from a deletion of promoter p415 (Belgian patent no. 901,222), (b) a SphI-BamHI fragment from plysΔ9 and comprising the complete cDNA of lysozyme, (c) an EcoRI-SphI fragment from plasmid pKO1 (K. Mc Kenney et al., in "Gene amplification and analysis", J. G. Chririkjan & T. Panas editors, Elsevier/North Holland, N.Y., 1981, p.383) to be used as a junction between fragments (b) and (d), (d) a PstI-EcoRI fragment from plasmid YEpZ415 comprising the origin of replication and one half of the β-lactamase gene of pBR322, and (e) a HindIII-PstI fragment from PJDB207 comprising the 2-micron-LEU2 segment and the other half of the β-lactamase gene. Before ligation, these various fragments were purified, and, since they carried different and complementary sticky ends, only one viable plasmid can result from this combination by legitimate ligation: plysΔ29 (FIG. 4).

By proceeding in the same way with two other fragments derived by deletion from promoter p415 (p415Δ4 and p415Δ5), two other plasmids were produced: plysΔ49 and plysΔ59. These three plasmids thus only differ by the fact that the promoter is positioned at various distances from the lysozyme cDNA, this resulting during transcription in different distances between the beginning (the 5' end) of the corresponding messenger RNAs and the natural AUG translation start site.

1.4. Lysozyme expression by plasmids plysΔ29, plysΔ49 and plysΔ59.

The plasmids constructed as described hereabove were then transformed into GRF18 strain (Leu−, His−) of the yeast S. cerevisiae, followed by selection for clones prototrophic for leucine (Leu+).

Figure 5:
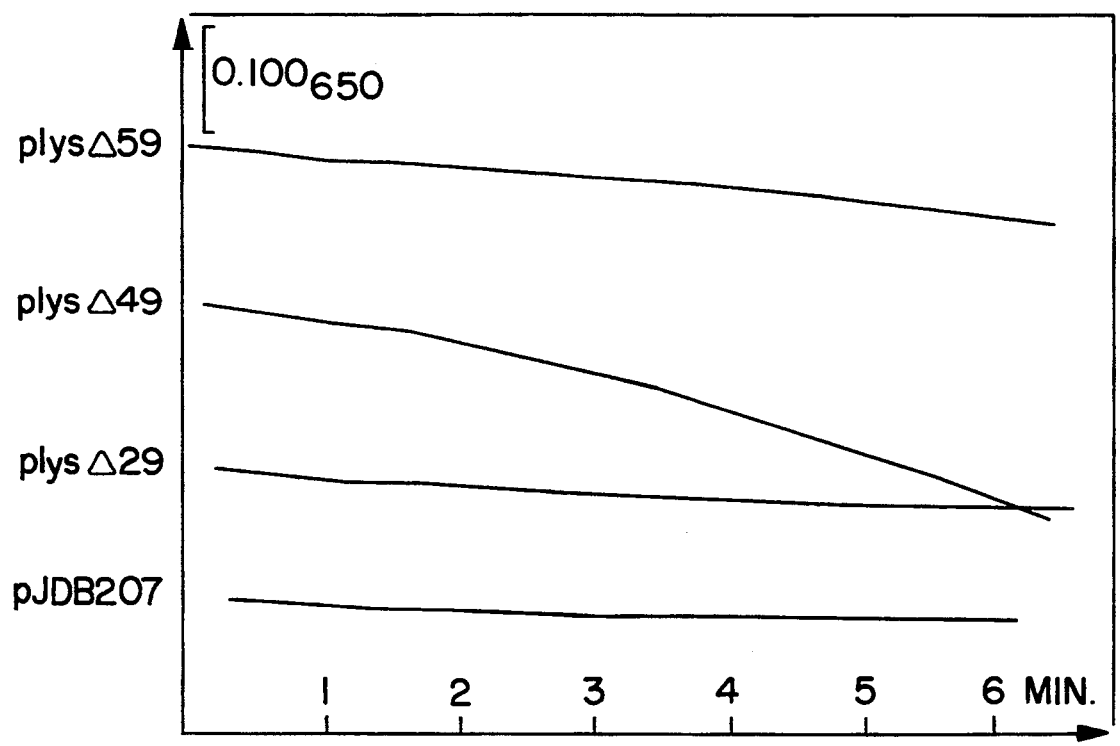
FIG. 5 shows that cellular extracts of yeasts transformed by plasmids plysΔ49 and plysΔ59 are capable of lysing E. coli cells treated with EDTA to make them susceptible to the action of lysozyme.

These clones were then ground with glass beads, and the obtained lysates were clarified by centrifugation. Their lysozyme activity was tested by determining the decrease in optical density of a suspension of E. coli cells by the method of Mc Macken et al. (J. Mol. Biol. 49, 1970, 639). In FIG. 5, the initial values of the optical density at 650 nm ($OD_{650}$) were identical for all clones (0.7), but they have been shifted on the diagram for clarity. The results of FIG. 5 show a significant activity for GRF18(plysΔ49), somewhat less for cells transformed by plasmid plysΔ59 and virtually none for those transformed by plysΔ29. Similar results were obtained by using a method in which the cells used as indicators for the action of lysozyme were those of the bacterium Micrococcus lysodeikticus (G. Alderton et al., J. Biol. Chem. 157, 1945, 43).

In a different type of assay, lysozyme was evidenced around transformed colonies growing on Petri dishes covered with a lawn of M. lysodeikticus. In this case, lysozyme expression was visualized by a transparent halo of bacterial lysis around the colonies. In agreement with the results using cell-free lysates, the halo of lysis was greatest with plysΔ49 indicating that this clone was the best producer of lysozyme. This result may also show that the lysozyme is exported from the yeast cell since it must of necessity be extracellular in order to lyse the bacterial indicator.

EXAMPLE 2

2.1. Construction of lysozyme expression vector plys50.

The vector pJDB207 upon which the lysozyme expression plasmids plysΔ29, plysΔ49 and plysΔ59 (described hereabove) are based, do not contain the entire 2-micron yeast plasmid and is consequently dependent on the presence of the endogenous 2-micron plasmid (found in most strains of S. cerevisiae) for its continued maintenance. This leads to such an unstable situation that the pJDB207-type plasmids are frequently lost from the cell (E. Erhaert & C. P. Hollenberg, J. Bacteriol. 156, 1983, 625, and M. Jarayam et al., Cell 34, 1983, 95). In contrast, the natural 2-micron plasmid is stably inherited. It is indeed known that plasmids constructed in such a way that they contain the entire 2-micron plasmid are more stable than those of the pJDB207-type (C. P. Hollenberg, Curr. Top. Microbiol. Immunol. 96, 1982, 119; R. M. Walmsley et al., Mol. Gen. Genet. 1983, 361). Such plasmids Such plasmids are therefore more useful for long term growth as, for example, in industrial fermentations.

Figure 6:
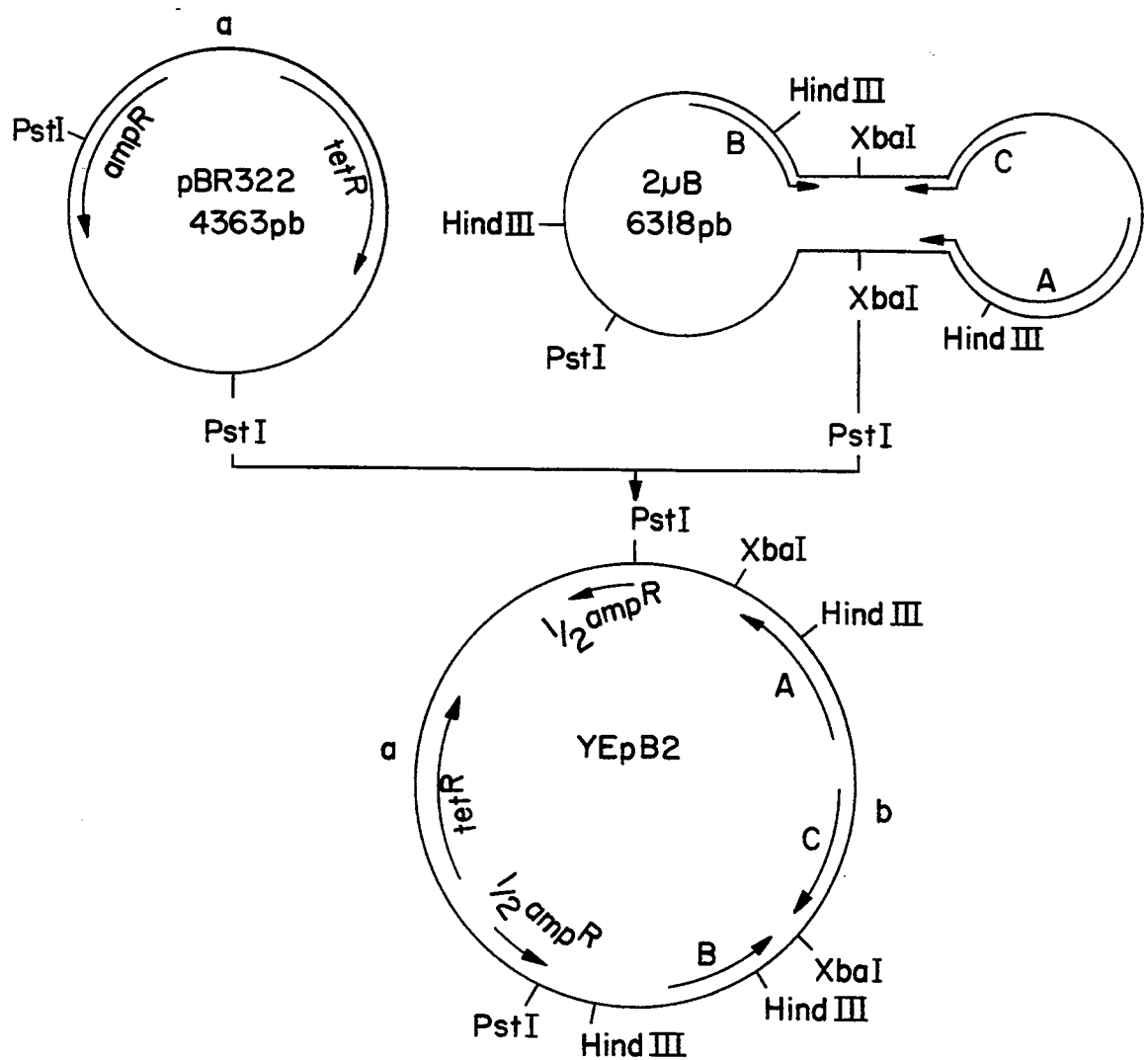
FIG. 6 represents the construction of plasmid YEpB2 by ligation of fragments obtained by the action of restriction enzyme PstI on plasmid pBR322 and on the 2-micron endogenous yeast plasmid.
Figure 7:
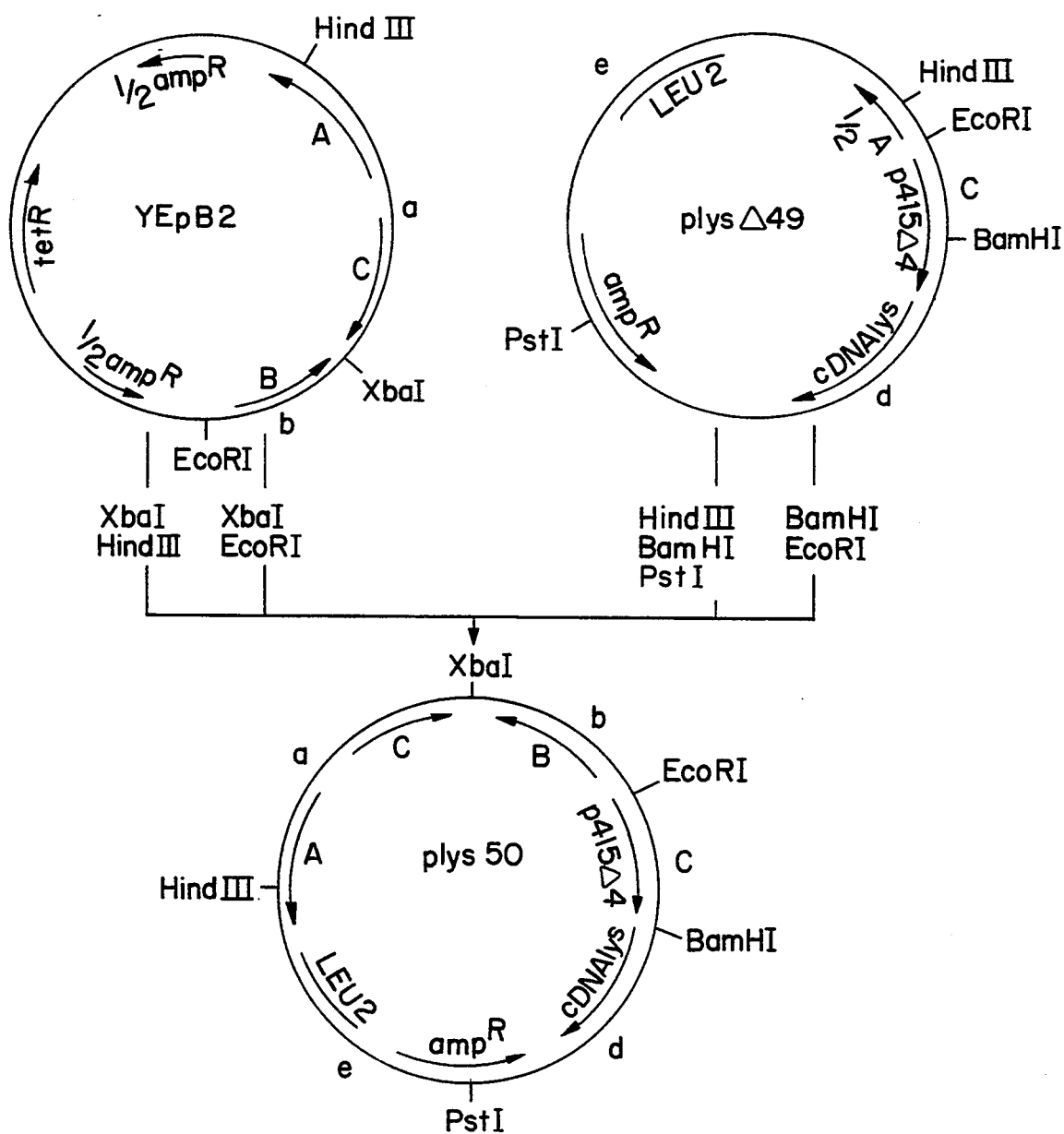
FIG. 7 represents the construction of the lysozyme expression vector plys50 by univocal ligation of five purified fragments obtained from plasmids YepB2 and plysΔ49.

To construct such a complete 2-micron vector, plasmid YEpB2 (FIG. 6) was used, which was previously made by cloning the entire 2-micron plasmid into pBR322 at their mutually unique PstI sites. Two fragments from YEpB2 and two fragments from plysΔ49 were then combined to give plys50 (FIG. 7). In this plasmid, the three 2-micron genes A, B and C are intact and the lysozyme gene is expressed from the p415Δ4 promoter as in plysΔ49 described in the preceeding example.

2.2. Expression of lysozyme by vector plys50.

After transforming the GRF18 strain (His−, Leu−) of S. cerevisiae by plasmids plys50 and pJDB207, the transformed cells obtained in both cases were separately grown on a minimum medium supplemented with histidine (0.002%). When the cultures had reached the stationary phase (cell dry weight=about 1.5 g/l of culture), the cells were separated from the culture medium by centrifugation, suspended in a 0.1M pH7 phosphate buffer, and ground with glass beads. Lysozyme activity in the supernatant and the lysate from both cultures was determined by their ability to lyse M. lysodeikticus cells according to the method of D. Shugar (Biochem. Biophys. Acta, 8, 1952, 302).

No lysozyme activity could be shown for the strain transformed by plasmid pJDB207. By contrast, in the case of GRF18(plys50) strain, an activity of 162 units per ml of culture was determined and shown to be distributed as follows: 44 units/ml associated with the cells and 118 units/ml in the medium.

By determining total proteins according to the method of D. Herbert et al. (Methods in Microbiol. 5B, 1971, 209) as modified by C. Wang and R. L. Smith (Anal. Biochem. 63, 1975, 414), taking into account the specific activity of commercial purified lysozyme (Boehringer Mannheim), it was determined that lysozyme produced by yeast in the above conditions accounts for about 1% of the soluble yeast proteins.

Strains GRF18(plysΔ49) and AH22cir°(plys50) were deposited on Dec. 5, 1984 at the Centraal Bureau voor Schimmelcultures, Oosterstraat 1, P.O. Box 273, NL-3740 AG Baarn (The Netherlands) where they have been respectively given accession numbers CBS 7130 and CBS 7129.

We claim:

1. A process for preparing lysozyme comprising the following steps:
   (a) growing in a culture medium Saccharomyces yeasts transformed with DNA comprising at least one copy of an expression cassette appropriately constructed for the expression of a 1,4-β-N-acetylmuramidase;
   (b) separating the yeast thus obtained from the culture medium; and
   (c) recovering the lysozyme present in said medium.

2. The process according to claim 1, wherein said lysozyme is produced such that it accounts for about 1% of the soluble yeast proteins.

3. A transformed Saccharomyces yeast containing DNA which comprises at least one copy of a fragment coding for a 1,4-β-N-acetylmuramidase, said fragment being expressed in said yeast as the corresponding active protein.

4. The transformed yeast according to claim 3, wherein the 5' end of said fragment is fused in frame with a leader sequence which causes said active protein to be secreted through the cytoplasmic membrane of the yeast cell.

5. The transformed yeast according to claim 4, wherein said leader sequence comprises the chicken lysozyme leader sequence.

6. The transformed yeast according to claim 3, wherein said fragment is inserted in a plasmid capable of autonomously replicating into a number of copies in said yeast.

7. The transformed yeast according to claim 6, wherein said plasmid carries a replication ensuring sequence of the 2-micron plasmid comprising at least the replication origin of said 2-micron plasmid.

8. The transformed yeast according to claim 3, wherein the 5' end of said fragment is fused with a strong yeast promoter for ensuring the efficient transcription thereof.

9. The transformed yeast according to claim 8, wherein said strong yeast promoter is selected from the group consisting of promoters of genes coding for alcohol dehydrogenase, enolase, glyceraldehyde-3-phosphate dehydrogenase, phosphoglycerate kinase alkaline phosphatase, promoter p415 and variants of promoter p415.

10. The transformed yeast according to claim 9, wherein said strong yeast promoter is selected from the group consisting of p415 and variants thereof.

11. The transformed yeast according to claim 6, wherein said yeast comprises a plasmid selected from the group consisting of plysΔ49 and plys50.

12. The transformed yeast according to claim 3, wherein said yeast belongs to the Saccharomyces cerevisiae species.

13. The transformed yeast according to claim 12, wherein said yeast is selected from the group consisting of strains GRF18 and AH22 of said species.

14. The transformed yeast according to claim 3, said yeast comprising yeast AH22 (plysΔ49).

15. The transformed yeast according to claim 3, said yeast comprising yeast AH22 (plys50).

16. The transformed yeast according to claim 3, said yeast comprising yeast GRF18 (plysΔ49).

17. The transformed yeast according to claim 3, said yeast comprising yeast GRF18 (plys50).

18. The transformed yeast according to claim 3, wherein said active protein accounts for about 1% of the soluble yeast proteins.

19. A Saccharomyces yeast which has been transformed by a plasmid comprising a lysozyme structural gene and which yeast secretes biologically active lysozyme upon expression of said gene.

20. A Saccharomyces yeast which has been transformed with a secretion vector comprising the chicken lysozyme leader sequence fused to a structural gene encoding lysozyme wherein said lysozyme gene may be the chicken lysozyme structural gene or a lysozyme structural gene from another species.

21. The transformed yeast according to claim 19, wherein the 5' end of the lysozyme structural gene is fused with a leader sequence which causes active lysozyme to be secreted through the cytoplasmic membrane of the yeast cell.

22. The transformed yeast according to claim 21, wherein said leader sequence comprises a chicken lysozyme leader sequence.

23. The transformed yeast according to claim 19, wherein said plasmid carries a replication-directing sequence derived from a 2-micron plasmid.

24. The transformed yeast of claim 23 wherein the replication-directing sequence comprises at least the replication origin of said 2-micron plasmid.

25. The transformed yeast according to claim 19, wherein the 5' end of said gene is fused with a yeast promoter.

26. The transformed yeast according to claim 25, wherein said yeast promoter is selected from the group consisting of promoters of genes coding for alcohol dehydrogenase, enolase, glyceraldehyde-3-phosphate dehydrogenase, phosphoglycerate kinase, alkaline phosphatase; promoter p415, and variants of promoter p415.

27. The transformed yeast according to claim 19, wherein said yeast comprises a plasmid selected from the group consisting of plys 49 and plys50.

28. The transformed yeast according to claim 19, wherein the biologically active lysozyme accounts for about 1% of the soluble yeast proteins.

29. The transformed yeast secretion vector according to claim 20, further defined as carrying a replication-directing sequence of a 2-micron plasmid.

30. The transformed yeast of claim 29 wherein the replication-directing sequence comprises at least the replication origin of said 2-micron plasmid.

31. The transformed yeast according to claim 20 wherein the secretion vector product accounts for about 1% of the soluble yeast.

32. A plasmid capable of autonomous replication in Saccharomyces yeast and comprising the genetic elements necessary for the expression in yeast of a DNA fragment coding for a 1,4-β-N-acetylmuramidase.

33. The plasmid according to claim 32, said plasmid carrying a replication ensuring sequence from a 2-micron plasmid comprising at least the replication origin of said 2-micron plasmid.

34. The plasmid according to claim 32, wherein said plasmid comprises a strong yeast promoter for ensuring expression of said DNA fragment.

35. The plasmid according to claim 34, wherein the strong yeast promoter is selected from the group consisting of promoters of genes coding for alcohol dehydrogenase, enolase, glyceraldehyde-3-phosphate dehydrogenase, phosphoglycerate kinase, alkaline phosphatase, promoter p415, and variants of promoter p415.

36. The plasmid according to claim 35, wherein the strong yeast promoter is selected from the group consisting of promoter p415 and variants thereof.

37. The plasmid according to claim 32, wherein said plasmid is selected from the group consisting of plasmids plysΔ49 and plys50.

38. The vector plasmid according to claim 32, wherein said DNA fragment is expressed such that it accounts for about 1% of the soluble yeast proteins.

* * * * *

UNITED STATES PATENT AND TRADEMARK OFFICE
CERTIFICATE OF CORRECTION

PATENT NO. : 5,336,609
DATED : August 9, 1994
INVENTOR(S) : Jacques Oberto, John R. N. Davison It is certified that error appears in the above-identified patent and that said Letters Patent is hereby corrected as shown below:

On the title page, item [22] should read:
    Filed: December 5, 1985

Signed and Sealed this

Seventeenth Day of August, 1999

Attest:

Q. TODD DICKINSON

*Attesting Officer*      *Acting Commissioner of Patents and Trademarks*